(12) United States Patent
Park

(10) Patent No.: US 7,905,849 B2
(45) Date of Patent: Mar. 15, 2011

(54) BACK BRACE FRAME WITH TWO INDIVIDUAL POWER MODULES

(76) Inventor: Dae Shik Park, Rowland Heights, CA (US)

( * ) Notice: Subject to any disclaimer, the term of this patent is extended or adjusted under 35 U.S.C. 154(b) by 286 days.

(21) Appl. No.: 12/321,804

(22) Filed: Jan. 26, 2009

(65) Prior Publication Data

US 2009/0204042 A1 Aug. 13, 2009

Related U.S. Application Data

(60) Provisional application No. 61/063,866, filed on Feb. 7, 2008.

(51) Int. Cl.
*A61F 5/00* (2006.01)
*A61F 5/37* (2006.01)
*A61B 19/00* (2006.01)
*A41F 19/00* (2006.01)

(52) U.S. Cl. ............ 602/19; 602/23; 128/876; 128/869; 2/309

(58) Field of Classification Search .................... 602/19, 602/20, 21, 22, 23, 32, 36, 60, 61, 15, 16, 602/5, 18; 128/95.1, 96.1, 100.1, 102.1, 128/874, 845, 846, 869, 876; 2/55, 57, 309; 601/122, 124

See application file for complete search history.

(56) References Cited

U.S. PATENT DOCUMENTS

| | | | |
|---|---|---|---|
| 3,889,664 A | 6/1975 | Heuser et al. |
| 4,752,982 A | 6/1988 | Jones et al. |
| 5,127,897 A | 7/1992 | Roller |
| 5,195,948 A | 3/1993 | Hill et al. |
| 5,399,150 A | 3/1995 | Saunders |
| 6,322,529 B1 | 11/2001 | Chung |
| 6,951,547 B1 | 10/2005 | Park et al. |
| 7,083,585 B2 | 8/2006 | Latham |

*Primary Examiner* — Patricia M Bianco
*Assistant Examiner* — Ophelia Hawthorne

(57) ABSTRACT

A waist support frame for a detachment type waist protecting belt to hold the vertebra region of a vertebra related patient is provided. The frame is comprised of two back rest frames, two Y-shape hinges, two power modules, two pullers, two sets of strings each of them are engaged and connects on one part (upper- or lower-part) of the two power modules, and two set of broad bands. Each power module is equipped with twelve pair of pulling code conveying mini rollers. String arrangement through these twelve pair of rollers enables the inventor to provide a waist support frame that can be used by a user whose one hand is not available without rotating the frame around the user's body with only one hand.

7 Claims, 8 Drawing Sheets

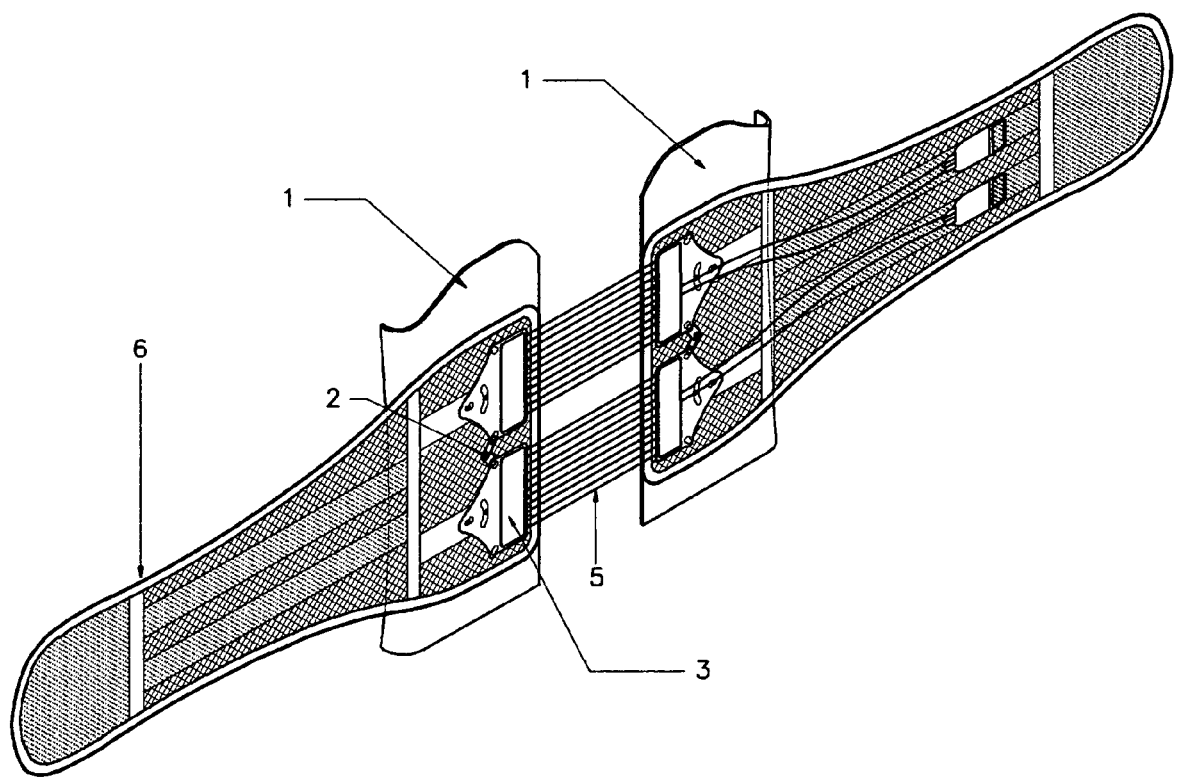
FIG. 1-a

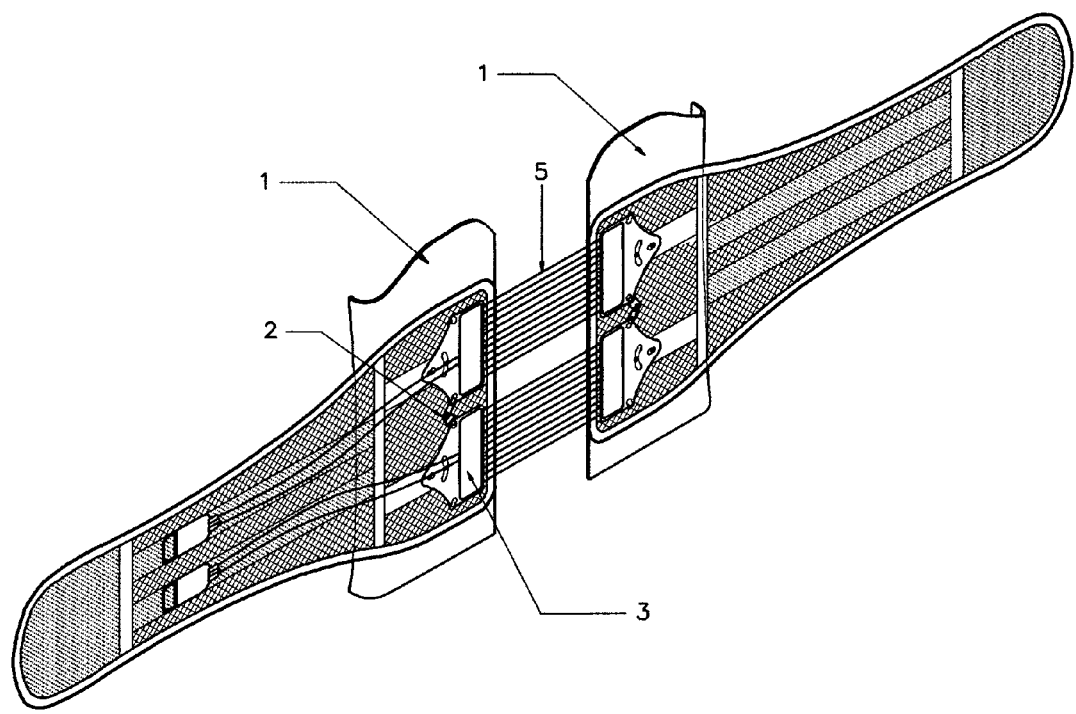
FIG. 1-b

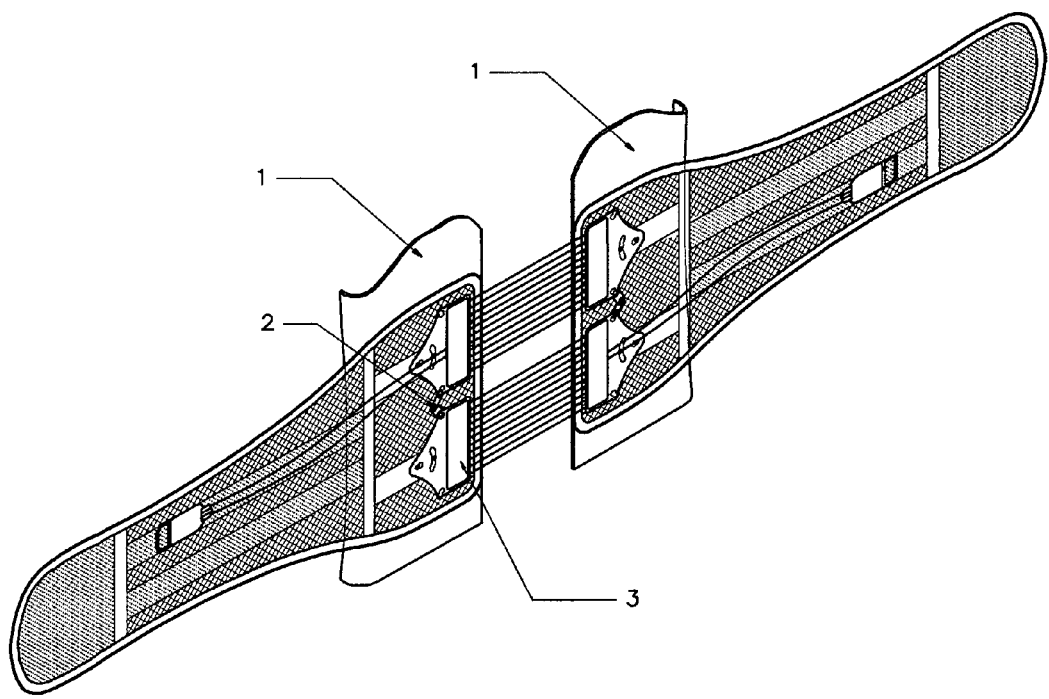
FIG. 1-c

BACK BRACE FRAME WITH TWO INDIVIDUAL POWER MODULES

Current application is non-provisional application of the provisional application of Application No. 61/063,866 which was filed on Feb. 7, 2008

FIELD OF THE INVENTION

The present invention relates to a waist support frame, more particularly, a frame enabling self-adjustment of the waist support frame to fit to the curvatures of a patient's with only one hand.

BACKGROUND OF THE INVENTION

As is well known in the industry, the waist-protecting belt, known as an abdominal support or a pelvic girdle, is comprised of a resilient belt made of a proper material such as spandex, and a rigid back supporting plate. The role of a waist-protecting belt is to slightly compress and support the waist of a vertebra related patient's body. This prevents pain by keeping the waist in straight vertical alignment. Adjusting the resilient belt controls pressure to the patient's back and body. However, the back supporting plate or frame, which directly touches the patient's back, is usually made of one rigid plate made of plastic or gypsum. Therefore, if the back supporting plate does not match the shape of the patient's back, it often causes undesired pain to the patient. A time consuming process of patterning the contour of a patient's back is necessary, to make the back supporting plate more effectively fit the curvature of the patient's back. It is purpose of the current application to provide a back brace frame that resolves all the previous drawbacks and especially provide a back brace frame that can be used by a patient whose one hand is not available.

DESCRIPTION OF THE PRIOR ARTS

U.S. Pat. No. 7,083,585 to Latham illustrates a string arrangement for a detachment type waist-protecting belt to hold the vertebra region of a vertebra related patient is provided. U.S. Pat. No. 6,951,547 to Park et al. illustrates a waist support frame for a detachment type waist protecting belt to hold the vertebra region of a vertebra related patient is provided. U.S. Pat. No. 6,322,529 to Chung illustrates a detachment type waist-protecting belt including a waist support, which fits a contour of the waist of the human body. The support is one-piece of solid material. U.S. Pat. No. 5,399,150 Saunders illustrates a lumbosacral back support band provided with a releasable attaching back support system, which is made of one piece of composite band. U.S. Pat. No. 5,195,948 to Hill, et al. illustrates a back support device comprised of a belt structure designed to fit substantially around the waist of a user. An inflatable air bladder is attached inside the belt structure so that it is positioned adjacent to the lower back when the back support device is worn. U.S. Pat. No. 5,127,897 to Roller illustrates a therapeutic back support device including a plastic back support plate, which is coupled to a human body to forwardly direct the plate. U.S. Pat. No. 4,752,982 to Jones, et al. illustrates an adjustable back support apparatus with an anchor assembly to adjustably connect the main support, and a cushion assembly connected to the main support base assembly. U.S. Pat. No. 3,889,664 to Heuser, et al. illustrates two torso belt members, joined together with a jack screw connector, intended to apply traction to the user between the pair of belts.

None of the prior arts introduces a back support plate, the shape of which is easily adjustable with the adjustment of a single strap even by a handicapped user.

SUMMARY OF THE INVENTION

As is well known in the industry, the waist-protecting belt, known as an abdominal support or a pelvic girdle, is comprised of a resilient belt made of a proper material such as spandex, and a rigid back supporting plate. The role of a waist-protecting belt is to slightly compress and support the waist of a vertebra related patient's body. This prevents pain by keeping the waist in straight vertical alignment. Adjusting the resilient belt controls pressure to the patient's back and body. However, the back supporting plate or frame, which directly touches the patient's back, is usually made of one rigid plate made of plastic or gypsum. Therefore, if the back supporting plate does not match the shape of the patient's back, it often causes undesired pain to the patient. A time consuming process of patterning the contour of a patient's back is necessary, to make the back supporting plate more effectively fit the curvature of the patient's back. It is purpose of the current application to provide a back brace frame that resolves all the previous drawbacks and especially provide a back brace frame that can be used by a patient whose one hand is not available. A waist support frame for a detachment type waist protecting belt to hold the vertebra region of a vertebra related patient is provided. The frame is comprised of two back rest frames, two Y-shape hinges, two power modules, two pullers, two sets of strings each of them are engaged and connects on one part (upper- or lower-part) of the two power modules, and two set of broad bands. Each power module is equipped with twelve pair of pulling code conveying mini rollers. String arrangement through these twelve pair of rollers enables the inventor to provide a waist support frame that can be used by a user whose one hand is not available without rotating the frame around the user's body with only one hand.

BRIEF DESCRIPTION OF THE DRAWINGS

FIG. 1-a is a perspective view of the back brace frame with two individual power modules according to current application when both of pullers are arranged to right hand side.

FIG. 1-b is a perspective view of the back brace frame with two individual power modules according to current application when both of pullers are arranged to left hand side.

FIG. 1-c is a perspective view of the back brace frame with two individual power modules according to current application when each of pullers are arranged to opposite hand side.

DETAILED DESCRIPTION OF THE PREFERRED EMBODIMENT

Figure 2:
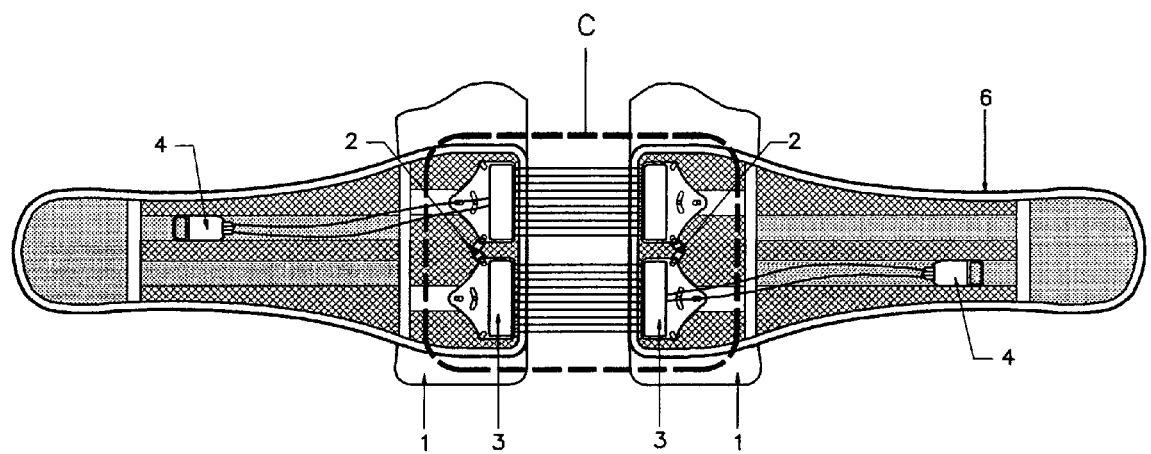
FIG. 2 is a front view of the back brace frame with two individual power modules according to current application when each of pullers are arranged to opposite hand side.

FIGS. 1-a and 1-b. show a perspective view of the back brace frame with two individual power modules according to current application. FIG. 1-*a* is a back brace frame for a user only right hand is available and FIG. 1-*b* is a back brace frame for a user only left hand is available. Meanwhile, FIG. 1-*c* shows a back brace frame for a user both hands are available. The back brace frame with two individual power modules according to current application is comprised of two back rest frames (1), two Y-shape hinges (2), two power modules (3), two pullers (4), two sets of strings (5) each of them are engaged and connects on one part (upper- or lower-part) of the two power modules (3), and two set of broad bands (6). FIG. 2 is a front view of the back brace frame with two individual power modules according to current application when each of pullers (4) are arranged to opposite hand side. This arrangement is for average patient who can use both hands.

Figure 3:
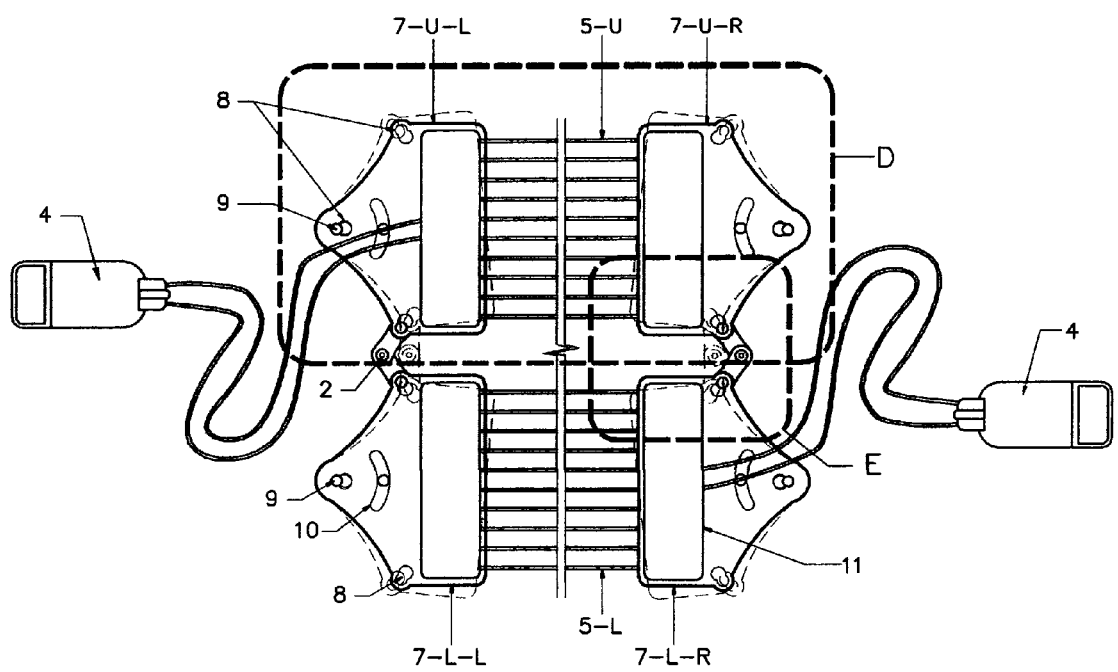
FIG. 3 is an enlarged view of the section 'C' in FIG. 2.

FIG. 3 is an enlarged view of the section 'C' in FIG. 2 showing details of the power module (3). Each power module (3) is comprised of two back brace plates (7) of upper- and lower-plate connected by a Y-shaped hinge (2). Two key holes (8) are developed on each plate (7) to receive two power module anchors (9) that are fixed on the back rest frame. One arc-shape angle adjust slot (10) is developed on the center of the plate (7) and receives another power module anchor (9). For one back brace frame, four back brace plates of (7-U-L), (7-U-R), (7-L-L) and (7-L-R) are used. Here, 7-U-L indicates upper left plate, 7-U-R indicates upper right plate, 7-L-L indicates lower left plate, and 7-L-R indicates lower right plate in FIG. 3. Upper plates of left and right side (7-U-L) and (7-U-R) are connected each other by a string (5-U) and by the same way lower plates of left and right side (7-L-L) and (7-L-R) connected by another string (5-L). Both ends of each ring are connected to one of the puller (4).

Figure 4:
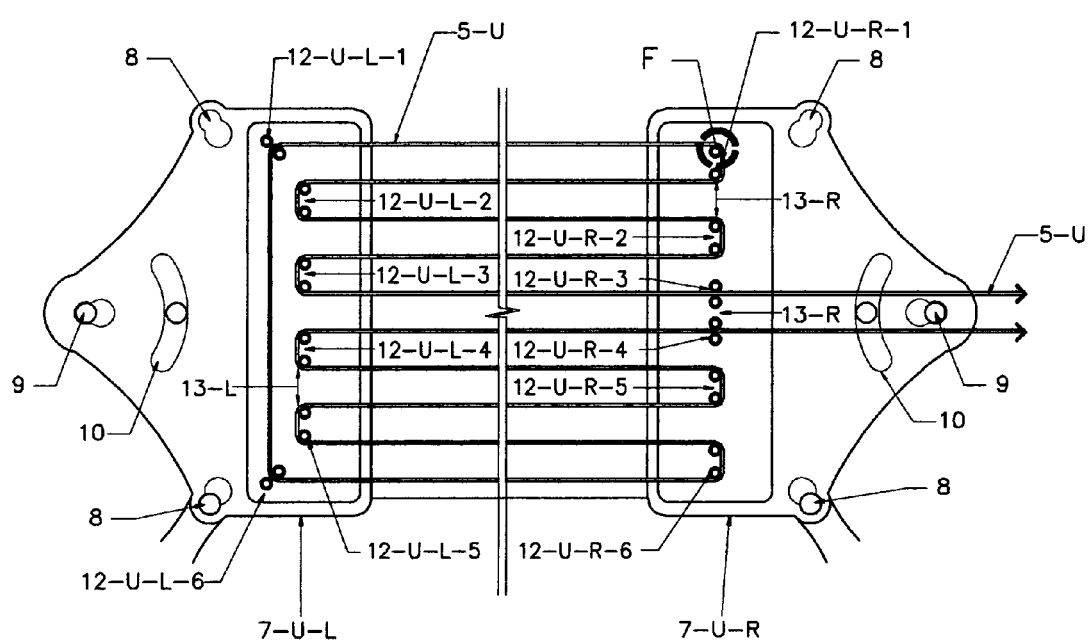
FIG. 4 is an enlarged view of the section 'D' in FIG. 3 showing the string arrangement that enables a handicapped user fasten the back brace without rotating of the back brace along the body of the user.

FIG. 4 is an enlarged view of the section 'D' in FIG. 3 showing the string's (5) arrangement that enables a handicapped user fasten the back brace without rotating of the back brace along the body of the user. This view is seen when both of the plastic covers (11) in the FIG. 3 are removed from the upper-plates of left and right (7-U-L), (7-U-R).

A single string (5-U) is engaged through 12 pairs of pulling code conveying mini rollers (12). The six pair of rollers, roller sets, installed on the upper plate of left side (7-U-L) is numbered as 12-U-L-1, 12-U-L-2, 12-U-L-3, 12-U-L-4, 12-U-L-5, and 12-U-L-6. The other six pairs of the rollers installed on the upper plate of right side (7-U-R) are numbered as 12-U-R-1, 12-U-R-2, 12-U-R-3, 12-U-R-4, 12-U-R-5, and 12-U-R-6. On the upper plate of left side (7-U-L), two roller sets (12-U-L-1) and (12-U-L-6), which constitute the upper most and lower most one, are located more left than the other four roller sets of (12-U-L-2), (12-U-L-3), (12-U-L-4) and (12-U-L-5). Those four roller sets (12-L-U-2) to (12-L-U-5) align in a row with same intervals (13-L).

Meanwhile, on the upper plate of right side (7-U-R), 6 roller sets align in a row. The upper two roller sets of (12-U-R-1), (12-U-R-2) and the lower two roller sets of (12-U-R-5)) and (12-U-R-5) are spaced with same interval (13-R) that is the same as the interval (13-L) on the left plate. Two roller sets of (12-U-R-3) and (12-U-R-4) that locate at the center has different interval (13-R') between them.

The string (5-U) passes through between the two roller of the roller set (12-U-L-1) and the two rollers of the roller set (12-U-L-6).

One side of the string (5-U) that passes through between the two rollers of the roller set (12-U-L-1) go around the roller set of (12-U-R-1) on the plate of right side (7-U-R) and then return to the plate of left side (7-U-L) to go around the roller set of (12-U-L-2). That side of the string keep on go around the roller sets of (12-U-R-2) and (12-U-L-3) in series and finally pass through between the two rollers of roller set (12-U-R-3).

The other side of the string (5-U) that passes through between the two rollers of the roller set (12-U-L-6) go around the roller set (12-U-R-6) on the plate of right side (7-U-R) and then return to the plate of left side (7-U-L) to go around the roller set of (12-U-L-5). That side of the string keep on go around the roller sets of (12-U-R-5) and (12-U-L-4) in series and finally pass through between the two rollers (12) of roller set (12-U-R-4).

Same configuration is applied to a lower back brace plates (7-L). Then, the combination is shown in FIG. 1-*a*. In this case, a user, whose left hand is not available, can fasten the bands (6) and the back rest frames (1) with only right hand. The string arrangement enables the user fasten the bands (6) and frames (1) without rotating them around the user's body.

Mirror image of the FIG. 4 creates a string arrangement for a user only left hand is available. If both of the upper and lower brace plates (7) have the mirror image of the FIG. 4, the result is shown in the FIG. 1-*b*, the bracelet for right hand handicapped user. For that case the upper plate of the right side has six pairs of rollers and the two roller sets, which constitute the upper most and lower most one, are located more left than the other four roller sets, which align in a row with same intervals. And the upper plate of the left side has six pair of rollers, which align in a row and the upper two roller sets and the lower two roller sets are spaced with same interval that is the same as the interval on the left plate and the rest two roller sets that locate at the center has different interval between them.

And the lower plate of the right side has six pairs of rollers and the two rollers sets, which constitute the upper most and lower most one, are located more left than the other four roller sets, which align in a row with same intervals.

And one lower plate of the left side has six pairs of rollers, which align in a row and the upper two roller sets and the lower two roller sets are spaced with same interval that is the same as the interval on the left plate. And the rest two roller sets that locate at the center has different interval between them.

For an average user, the configuration is shown in the FIG. 1-*c*. Both hands are available. In that case the arrangement of rollers are different in each neighboring plates. Followings are the examples.

If the upper plate of the left side has six pairs of rollers and the two roller sets, which constitute the upper most and lower most one, are located more left than the other four roller sets, which align in a row with same intervals. And the upper plate of the right side has six pair of rollers, which align in a row and the upper two roller sets and the lower two roller sets are spaced with same interval that is the same as the interval on the left plate and the rest two roller sets that locate at the center has different interval between them. And the lower plate of the right side has six pairs of rollers and the two roller sets, which constitute the upper most and lower most one, are located more left than the other four roller sets, which align in a row with same intervals. And one lower plate of the left side has six pairs of rollers, which align in a row and the upper two roller sets and the lower two roller sets are spaced with same interval that is the same as the interval on the left plate. And the rest two roller sets that locate at the center has different interval between them.

The other case is that the upper plate of the right side has six pairs of rollers and the two roller sets, which constitute the upper most and lower most one, are located more left than the other four roller sets, which align in a row with same intervals.

And the upper plate of the left side has six pair of rollers, which align in a row and the upper two roller sets and the lower two roller sets are spaced with same interval that is the same as the interval on the left plate and the rest two roller sets that locate at the center has different interval between them. And the lower plate of the right side has six pairs of rollers and the two roller sets, which constitute the upper most and lower most one, are located more left than the other four roller sets, which align in a row with same intervals. And one lower plate of the left side has six pairs of rollers, which align in a row and the upper two roller sets and the lower two roller sets are spaced with same interval that is the same as the interval on the left plate. And the rest two roller sets that locate at the center has different interval between them.

Figure 5:
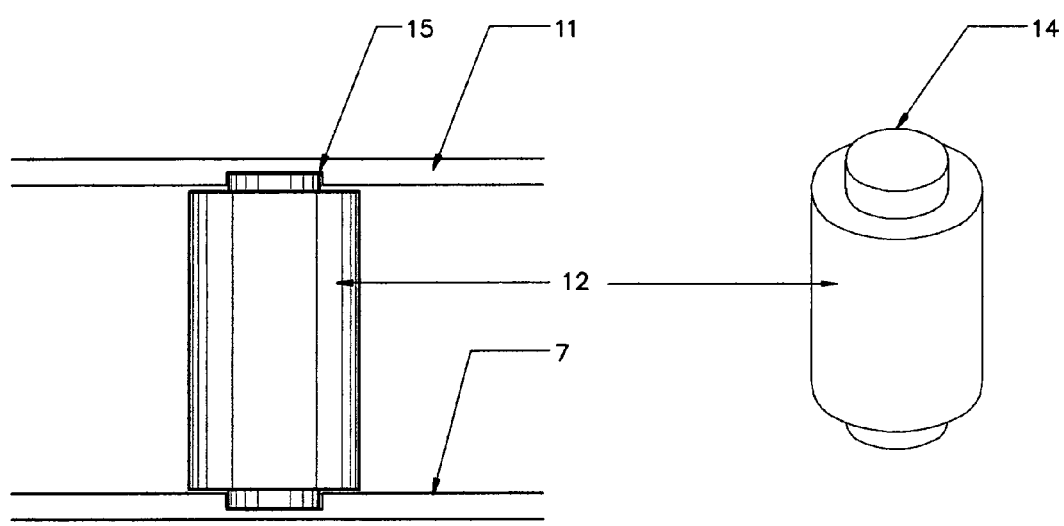
FIG. 5 is a detailed view of the pulling cord conveys mini roller.

FIG. 5 is a detailed view of the pulling cord conveys mini roller that comprises the roller sets (12). The rollers (12) are placed between the back brace plate (7) and the plastic cover (11). The roller (12) is made of brass rod that has protrusions (14) that are engaged to the grooves (15) which are developed on the back brace plate (7) and the plastic cover (11). The material of brass that constitute the roller (12) and the material of plastic that constitute the back brace plate (7) the plastic cover have minimum friction coefficient and endurance.

Figure 6:
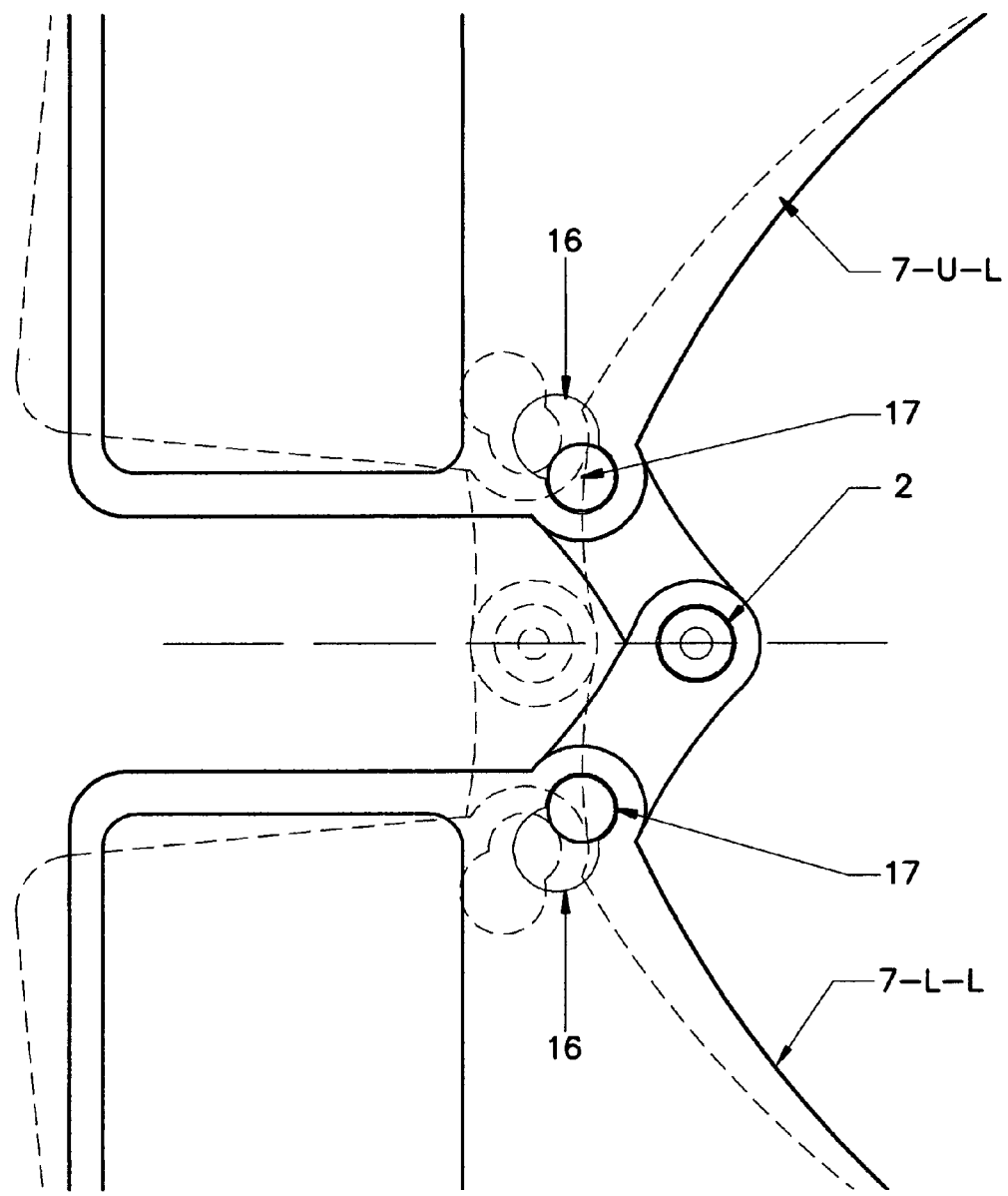
FIG. 6 is an enlarged view of the section 'E' of the back brace that enables fastening various body shape of a user.

FIG. 6 is an enlarged view of the section 'E' of the back brace that enables fastening various body shape of a user. The Y-Shape hinge (2) connects the upper plate of the left side (7-U-L) and the lower plate of the left side (7-L-L). Though not shown in the FIG. 6, same structure is applied for the upper- and lower-plate of the right side (7-U-R), L-R) as shown in the FIGS. 1-a to 1-c. Key holes (16) developed on the both of the plates receive the keys (17) that are developed on the both ends of the Y-shape hinge (2). The key holes (16) have 'connected circles' shape to allow the plates (7) adjusted to the various shape of the upper-body and lower body of the user.

What is claimed is:

1. A waist support frame for a detachment type waist protecting belt to hold the vertebra region of a vertebra related patient, whose one hand is not available, without rotating the flame around the user's body with only one hand is comprised of;
    two back rest frames, and
    two Y-shape hinges, and
    two power modules, each of which is comprised of two back brace plates of upper- and lower-plate, each of them has two key holes developed to receive two power module anchors that are fixed on the back rest frame and has one arc-shape angle adjust slot, developed on the center of the plate to receive another power module anchor, and are connected by the Y-shape hinge, and
    each of which is equipped with twelve pairs of pulling code conveying mini rollers, and
    two pullers, and
    an upper string that is engaged and connected to the upper-parts of the two power modules and both ends of the string are connected to one of the pullers, and a lower string that is engaged and connected to the lower-parts of the two power
    modules and both ends of the string are connected to one of the pullers, and two set of broad bands.

2. A waist support frame for a detachment type waist protecting belt to hold the vertebra region of a vertebra related patient, whose one hand is not available, without rotating the frame around the user's body with only one hand of claim 1, wherein;
    the two power modules are comprised of one left module and one right module and divided into four plates of one upper plate of the left side, one upper plate of right side, one lower plate of the left side, and one lower plate of the right side, and
    an upper string that is engaged and connected to the upper-parts of the two power modules and both ends of the string are connected to one of pullers, and
    a lower string that is engaged and connected to the lower-parts of the two power modules and both ends of the string are connected to one of pullers.

3. A waist support frame for a detachment type waist protecting belt to hold the vertebra region of a vertebra related patient, whose one hand is not available, without rotating the frame around the user's body with only one hand of claim 2,
    wherein each plate is equipped with six pairs of pulling code conveying mini rollers and
    an upper string that is engaged and connected to the upper-parts of the two power modules and both ends of the string are connected to one of pullers, and
    a lower string that is engaged and connected to the lower-parts of the two power modules and both ends of the string are connected to one of pullers.

4. A waist support frame for a detachment type waist protecting belt to hold the vertebra region of a vertebra related patient, whose one hand is not available, without rotating the frame around the user's body with only one hand of claim 2,
    the upper plate of the left side has six pairs of rollers and the two roller sets, which constitute the upper most and lower most one, are located more left than the other four roller sets, which align in a row with same intervals, and
    the upper plate of the right side has six pair of rollers, which align in a row and the upper two roller sets and the lower two roller sets are spaced with same interval that is the same as the interval on the left plate, and the rest two roller sets that locate at the center has different interval between them,
    and
    the lower plate of the left side has six pairs of rollers and the two roller sets, which constitute the upper most and lower most one, are located more left than the other four roller sets, which align in a row with same intervals, and
    one lower plate of the right side has six pairs of rollers, which align in a row and the upper two roller sets and the lower two roller sets are spaced with same interval that is the same as the interval on the left plate, and the rest two roller sets that locate at the center has different interval between them for a user whose left hand is not available.

5. A waist support frame for a detachment type waist protecting belt to hold the vertebra region of a vertebra related patient, whose one hand is not available, without rotating the frame around the user's body with only one hand of claim 2,
    the upper plate of the right side has six pairs of rollers and the two roller sets, which constitute the upper most and lower most one, are located more left than the other four roller sets, which align in a row with same intervals, and
    the upper plate of the left side has six pair of rollers, which align in a row and the upper two roller sets and the lower two roller sets are spaced with same interval that is the same as the interval on the left plate, and the rest two roller sets that locate at the center has different interval between them,
    and the lower plate of the right side has six pairs of rollers and the two roller sets, which constitute the upper most and lower most one, are located more left than the other four roller sets, which align in a row with same intervals, and one lower plate of the left side has six pairs of rollers, which align in a row and the upper two roller sets and the lower two roller sets are spaced with same interval that is the same as the interval on the left plate, and the rest two roller sets that locate at the center has different interval between them for a user whose right hand is not available.

6. A waist support frame for a detachment type waist protecting belt to hold the vertebra region of a vertebra related patient, whose one hand is not available, without rotating the frame around the user's body with only one hand of claim 2, the upper plate of the left side has six pairs of rollers and the two roller sets, which constitute the upper most and lower most one, are located more left than the other four roller sets, which align in a row with same intervals, and the upper plate of the right side has six pair of rollers, which align in a row and the upper two roller sets and the lower two roller sets are spaced with same interval that is the same as the interval on the left plate, and the rest two roller sets that locate at the center has different interval between them, and the lower plate of the right side has six pairs of rollers and the two roller sets, which constitute the upper most and lower most one, are located more left than the other four roller sets, which align in a row with same intervals, and one lower plate of the left side has six pairs of rollers, which align in a row and the upper two roller sets and the lower two roller sets are spaced with same interval that is the same as the interval on the left plate, and the rest two roller sets that locate at the center has different interval between them for a user whose both hands are available.

7. A waist support frame for a detachment type waist protecting belt to hold the vertebra region of a vertebra related patient, whose one hand is not available, without rotating the frame around the user's body with only one hand of claim 2, the upper plate of the right side has six pairs of rollers and the two roller sets, which constitute the upper most and lower most one, are located more left than the other four roller sets, which align in a row with same intervals, and the upper plate of the left side has six pair of rollers, which align in a row and the upper two roller sets and the lower two roller sets are spaced with same interval that is the same as the interval on the left plate, and the rest two roller sets that locate at the center has different interval between them, and the lower plate of the right side has six pairs of rollers and the two roller sets, which constitute the upper most and lower most one, are located more left than the other four roller sets, which align in a row with same intervals, and one lower plate of the left side has six pairs of rollers, which align in a row and the upper two roller sets and the lower two roller sets are spaced with same interval that is the same as the interval on the left plate, and the rest two roller sets that locate at the center has different interval between them for a user whose both hands are available.

* * * * *